US00PP22738P2

(12) United States Plant Patent
Blom

(10) Patent No.: US PP22,738 P2
(45) Date of Patent: May 15, 2012

(54) *CAMPANULA* PLANT NAMED 'FREYA'

(50) Latin Name: *Campanula glomerata*
Varietal Denomination: Freya

(76) Inventor: Arie Blom, Vleuten (NL)

( * ) Notice: Subject to any disclaimer, the term of this patent is extended or adjusted under 35 U.S.C. 154(b) by 18 days.

(21) Appl. No.: 12/807,251

(22) Filed: Aug. 31, 2010

(51) Int. Cl.
*A01H 5/00* (2006.01)

(52) U.S. Cl. ..... Plt./414

(58) Field of Classification Search ..... Plt./414
See application file for complete search history.

*Primary Examiner* — June Hwu
(74) *Attorney, Agent, or Firm* — C. A. Whealy

(57) ABSTRACT

A new and distinct cultivar of *Campanula* plant named 'Freya', characterized by its upright plant habit; freely basal branching habit; freely flowering habit; and dark violet-colored campanulate-shaped flowers.

3 Drawing Sheets

Botanical designation: *Campanula glomerata.*
Cultivar denomination: 'FREYA'.

BACKGROUND OF THE INVENTION

The present invention relates to a new and distinct cultivar of *Campanula* plant, botanically known as *Campanula glomerata* and hereinafter referred to by the name 'Freya'.

The new *Campanula* is a product of a planned breeding program conducted by the Inventor in IJsselstein, The Netherlands. The objective of the breeding program is to create new compact and freely flowering *Campanula* plants with attractive flower color.

The new *Campanula* plant originated from an open-pollination in IJsselstein, The Netherlands in May, 2004, of a proprietary selection of *Campanula glomerata* identified as code number Ca 406-02, not patented, as the female, or seed, parent with an unknown selection of *Campanula glomerata* as the male, or pollen, parent. The new *Campanula* was discovered and selected by the Inventor as a single flowering plant from within the progeny of the stated open-pollination grown in a controlled greenhouse environment in Zuidwolde, The Netherlands in June, 2008.

Asexual reproduction of the new *Campanula* plant by tissue culture in The Netherlands, since October, 2008, has shown that the unique features of this new *Campanula* plant are stable and reproduced true to type in successive generations.

SUMMARY OF THE INVENTION

Plants of the new *Campanula* have not been observed under all possible environmental conditions. The phenotype may vary somewhat with variations in environment such as temperature and light intensity without, however, any variance in genotype.

The following traits have been repeatedly observed and are determined to be the unique characteristics of 'Freya'. These characteristics in combination distinguish 'Freya' as a new and distinct cultivar:

1. Upright plant habit.
2. Freely basal branching habit.
3. Freely flowering habit.
4. Dark violet-colored campanulate-shaped flowers.

Plants of the new *Campanula* differ from plants of the female parent selection in the following characteristics:

1. Plants of the new *Campanula* are more compact than plants of the female parent selection.
2. Plants of the new *Campanula* have stronger stems than plants of the female parent selection.
3. Plants of the new *Campanula* are more freely flowering than plants of the female parent selection.

Plants of the new *Campanula* can be compared to plants of *Campanula* 'Acaulis', not patented. In side-by-side comparisons conducted in IJsselstein, The Netherlands, plants of the new *Campanula* differed from plants of 'Acaulis' in the following characteristics:

1. Plants of the new *Campanula* were more compact than plants of 'Acaulis'.
2. Plants of the new *Campanula* were more freely basal branching than plants of 'Acaulis'.
3. Plants of the new *Campanula* had smaller flowers than plants of 'Acaulis'.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the actual colors of the new *Campanula* plant.

The photograph on the first sheet is a side perspective view of a typical flowering plant of 'Freya' grown in a container.

The photograph on the second sheet is a close-up view of a typical leaf of 'Freya'.

The photograph on the third sheet is a close-up view of a typical inflorescence of 'Freya'.

DETAILED BOTANICAL DESCRIPTION

Plants used for the aforementioned photographs and following description were grown under conditions which closely approximate commercial production conditions during the spring and early summer in 13-cm containers (photographs) and ground beds (description) in an outdoor nursery in Zuidwolde, The Netherlands. During the production of the plants, day temperatures ranged from 15° C. to 30° C. and night temperatures ranged from 6° C. to 18° C. Plants were two years old when the photographs and description were taken. In the following description, color references are made to The Royal Horticultural Society Colour Chart, 2007 Edition, except where general terms of ordinary dictionary significance are used.

Botanical classification: *Campanula glomerata* 'Freya'.

Parentage:

*Female parent.*—Proprietary selection of *Campanula glomerata* identified as code number Ca 406-02, not patented.

*Male parent.*—Unknown selection of *Campanula glomerata,* not patented.

Propagation:

*Type.*—By tissue culture.

*Time to initiate roots.*—About ten days at 25° C.

*Time to produce a rooted young plant.*—About 35 days at 21° C.

*Root description.*—Fine, fibrous; pale cream in color.

*Rooting habit.*—Freely branching; dense.

Plant description:

*Form.*—Herbaceous perennial; upright plant habit; freely basal branching habit with about 27 basal branches developing per plant; moderately vigorous growth habit; campanulate flowers arranged in compound racemes.

*Plant height.*—About 50.5 cm.

*Plant width.*—About 41.1 cm.

*Basal branch description.*—Aspect: About 10° from vertical. Length (to top of foliar plane): About 41 cm. Length (to top of inflorescences): About 50.5 cm. Diameter: About 4.5 mm. Internode length: About 3.4 cm. Strength: Strong. Texture: Sparsely pubescent. Color: Close to 144A to 144B tinged with close to 178A to 178B.

Foliage description:

*Arrangement.*—Alternate, simple.

*Length.*—About 8.4 cm.

*Width.*—About 3.2 cm.

*Shape.*—Ovate to narrowly ovate.

*Apex.*—Broadly acute.

*Base.*—Basal leaves, cordate to attenuate; upper leaves, cuneate.

*Margin.*—Irregularly serrate.

*Texture, upper and lower surfaces.*—Sparsely pubescent; rough.

*Venation pattern.*—Pinnate.

*Color.*—Developing leaves, upper surface: Close to 137A and N137C; towards the base, close to 144A. Developing leaves, lower surface: Close to 137B; towards the base, close to 144A. Fully expanded foliage, upper surface: Close to N137A; venation, 144B to 144C. Fully expanded foliage, lower surface: Close to 137C; venation, close to 145A.

*Petiole length.*—About 8.5 cm.

*Petiole diameter.*—About 2.5 mm.

*Petiole texture, upper and lower surfaces.*—Sparsely pubescent.

*Petiole color, upper and lower surfaces.*—Close to 144A.

Flower description:

*Flower arrangement and shape.*—Single campanulate star-shaped flowers arranged in compound racemes; flowers face mostly outwardly to drooping; freely flowering habit, about 18 flowers develop per terminal inflorescence and about nine flowers develop per axillary inflorescence.

*Natural flowering season.*—Continuous flowering from late May to early August in The Netherlands.

*Flower longevity on the plant.*—About ten days; flowers persistent.

*Fragrance.*—None detected.

*Flower buds.*—Length: About 1.2 cm. Diameter: About 6 mm. Shape: Obovate. Color: Close to N187D.

*Flowers.*—Diameter: About 2.2 cm. Depth (height): About 2.1 cm.

*Petals.*—Arrangement: Five in a single whorl; fused. Length: About 2 cm. Width: About 6 mn. Shape: Narrowly obovate. Apex: Acute. Margin: Entire. Texture, upper surface: Pubescent. Texture, lower surface: Smooth, glabrous. Color: When opening, upper surface: Close to 83D; towards the base, close to N87C to N87D. When opening, lower surface: Close to N87C to N87D. Fully opened, upper surface: Close to N87A; towards the base, close to N87C to N87D; venation, similar to surface color; color becoming close to N88A with development. Fully opened, lower surface: Close to N87B; towards the base, close to N87C; venation, similar to surface color.

*Sepals.*—Arrangement: Five in a single campanulate whorl; fused. Length: About 1.2 cm. Width: About 3 mm. Shape: Lanceolate. Apex: Narrowly acute. Margin: Entire. Texture, upper and lower surfaces: Pubescent. Color, immature, upper and lower surfaces: Close to 144A; towards the base, close to 150C. Color, mature, upper surface: Close to 144A; towards the base, close to 144C. Color, mature, lower surface: Close to 143B; towards the base, close to 144A.

*Pedicels.*—Length: About 2 mm. Diameter: About 1.5 mm. Aspect: Upright. Strength: Strong. Texture: Pubescent. Color: Close to 144C.

*Reproductive organs.*—Stamens: Quantity per flower: Five. Anther shape: Narrowly lanceolate. Anther length: About 8 mm. Anther color: Close to 4B. Filament length: About 2 mm. Filament color: Close to N155C. Pollen amount: Moderate. Pollen color: Close to 4D. Pistils: Quantity per flower: One. Pistil length: About 1.7 cm. Stigma shape: Narrowly lanceolate. Stigma color: Close to 157A. Style length: About 1.5 cm. Style color: Close to 157D; towards the base, close to NN155D. Ovary color: Close to 145B.

*Seed/fruit.*—Seed and fruit production have not been observed.

Disease/pest resistance: Plants of the new *Campanula* have not been noted to be resistant to pathogens and pests common to *Campanula.*

Garden performance: Plants of the new *Campanula* have exhibited good tolerance to rain and wind, are hardy to USDA Hardiness Zone 3 and have been observed to tolerate high temperatures of about 35° C.

It is claimed:

1. A new and distinct *Campanula* plant named 'Freya' as illustrated and described.

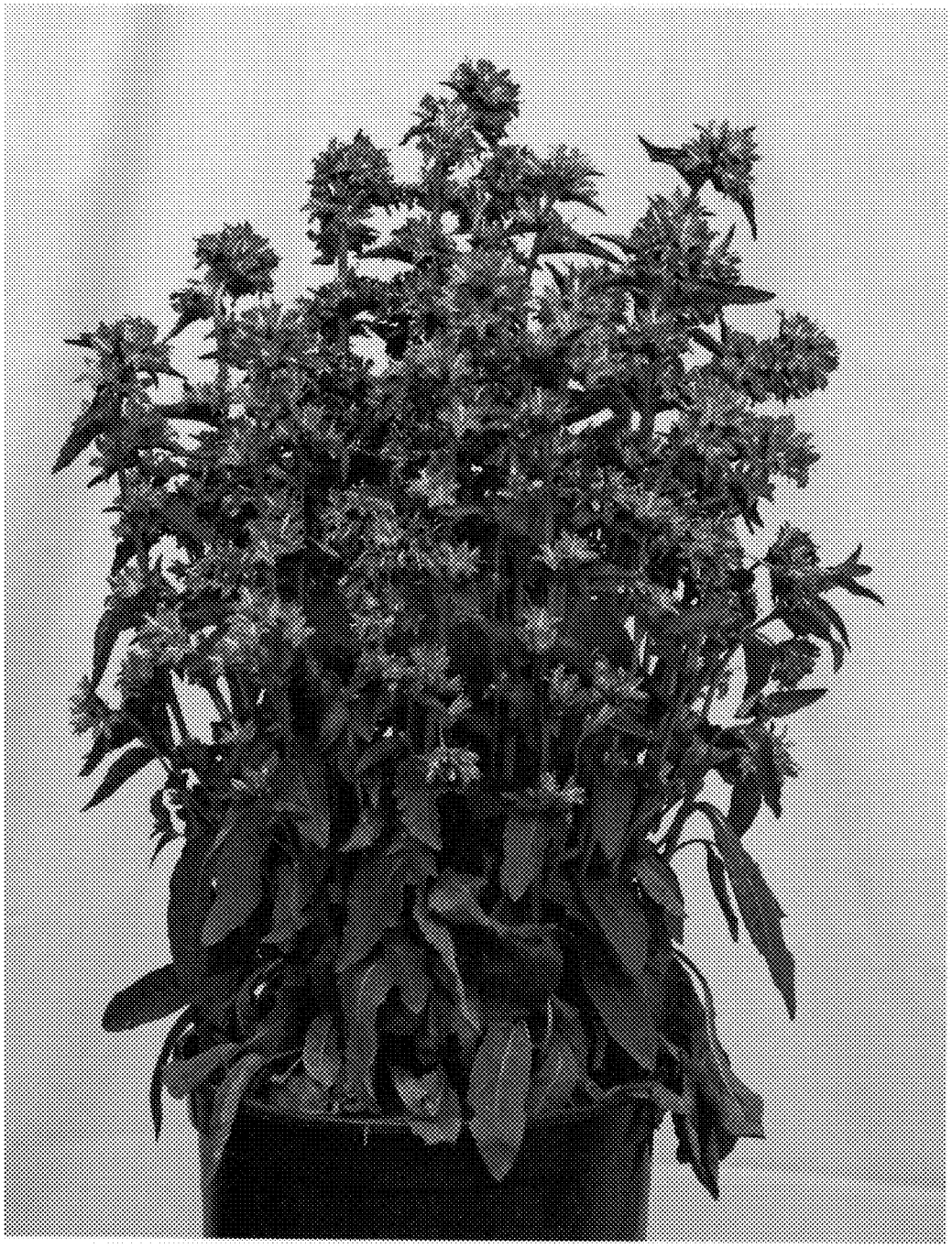

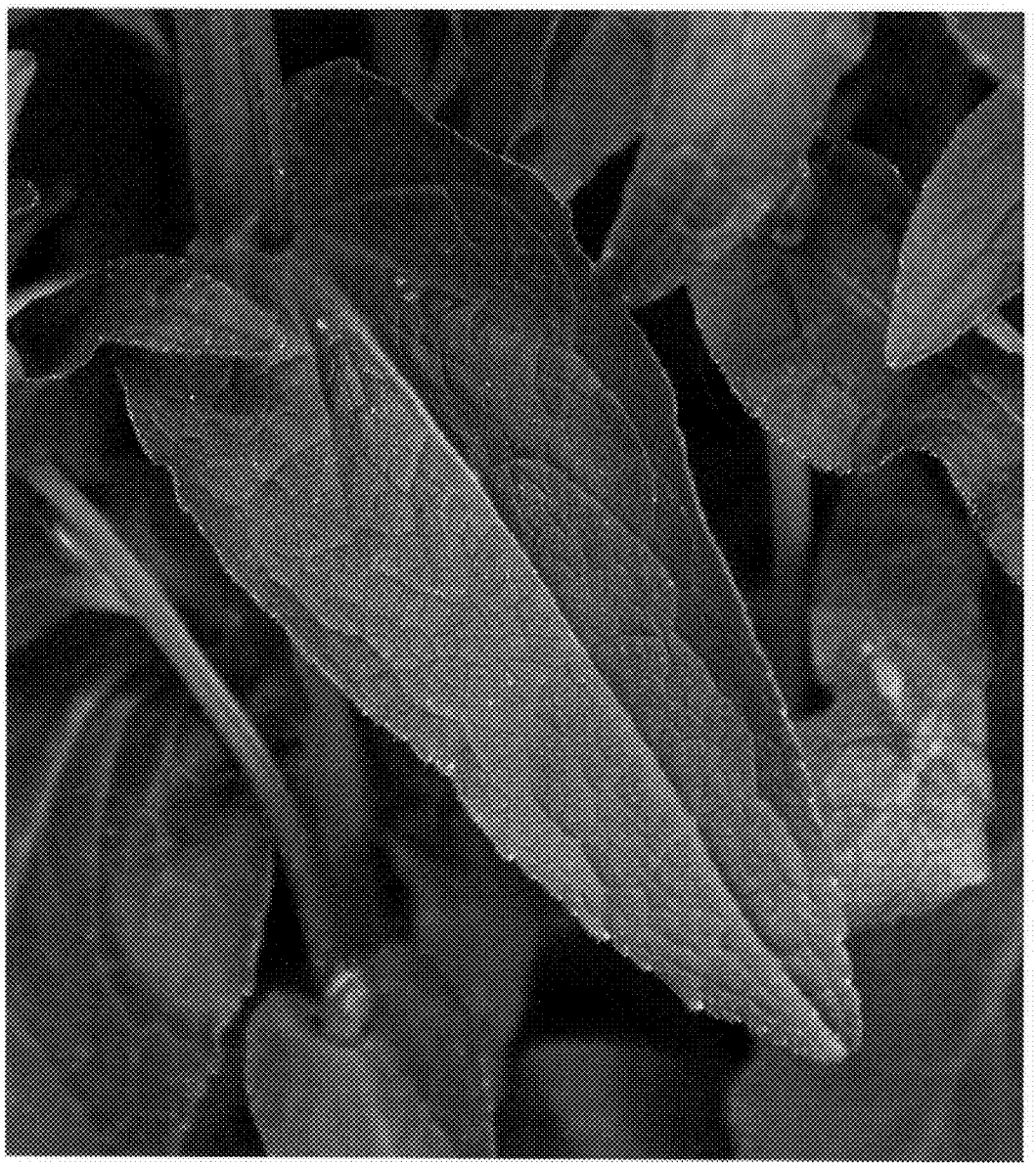

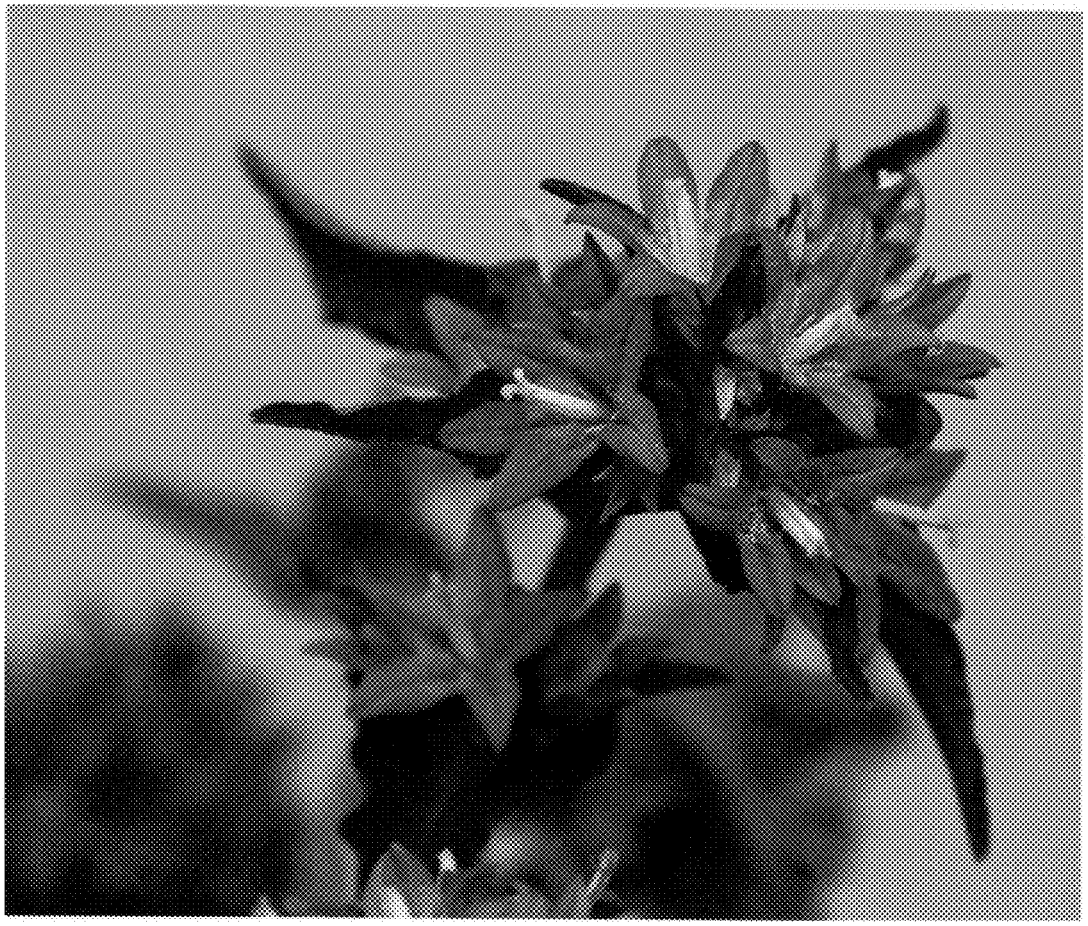

* * * * *